US009138168B2

(12) United States Patent
Casale et al.

(10) Patent No.: US 9,138,168 B2
(45) Date of Patent: Sep. 22, 2015

(54) APPARATUS AND METHOD FOR VIDEORHINOHYGROMETRIC (VRI) MEASURES

(75) Inventors: Manuele Casale, Rome (IT); Fabrizio Salvinelli, Rome (IT); Roberto Setola, Rome (IT); Paolo Soda, Rome (IT); Valerio Cusimano, Rome (IT)

(73) Assignee: UNIVERSITA CAMPUS BIO-MEDICO DI ROMA (IT)

( * ) Notice: Subject to any disclaimer, the term of this patent is extended or adjusted under 35 U.S.C. 154(b) by 1096 days.

(21) Appl. No.: 12/296,870

(22) PCT Filed: Apr. 13, 2006

(86) PCT No.: PCT/IT2006/000251
§ 371 (c)(1),
(2), (4) Date: May 1, 2009

(87) PCT Pub. No.: WO2007/119252
PCT Pub. Date: Oct. 25, 2007

(65) Prior Publication Data
US 2009/0221927 A1    Sep. 3, 2009

(51) Int. Cl.
*A61B 5/08*    (2006.01)
*A61B 5/087*    (2006.01)
*A61B 5/085*    (2006.01)

(52) U.S. Cl.
CPC ............. *A61B 5/0873* (2013.01); *A61B 5/0803* (2013.01); *A61B 5/085* (2013.01); *A61B 5/0816* (2013.01)

(58) Field of Classification Search
USPC .......................................... 600/529, 532, 543
See application file for complete search history.

(56) References Cited

U.S. PATENT DOCUMENTS

| 4,128,317 | A | * | 12/1978 | LeCover ..................... 351/245 |
| 4,174,900 | A | * | 11/1979 | Ina .............................. 248/163.1 |
| 4,318,082 | A | * | 3/1982 | King ............................ 382/282 |
| 4,443,837 | A | * | 4/1984 | Migliori et al. ............... 362/396 |
| 4,530,584 | A | * | 7/1985 | Schmidt ....................... 396/428 |
| 4,945,919 | A | * | 8/1990 | Hattori ......................... 600/549 |
| 5,023,755 | A | * | 6/1991 | Rosenberg ..................... 362/12 |
| 5,364,024 | A | * | 11/1994 | Lin .............................. 236/44 C |
| 5,676,154 | A | | 10/1997 | Pettersson |
| 6,690,814 | B1 | * | 2/2004 | Yuasa et al. .................. 382/118 |
| 7,413,305 | B2 | * | 8/2008 | Baumann et al. ............. 351/208 |
| 2004/0211868 | A1 | * | 10/2004 | Holmes et al. ........... 248/231.71 |
| 2006/0072158 | A1 | * | 4/2006 | Christie ...................... 358/3.01 |

FOREIGN PATENT DOCUMENTS

JP    10080415 A    *    3/1998

OTHER PUBLICATIONS

Cocks, Improved Glatzel Mirror, 1915, New York Academy of Medicine, pp. 135-141.*

(Continued)

*Primary Examiner* — Navin Natnithithadha
*Assistant Examiner* — Michael R Bloch
(74) *Attorney, Agent, or Firm* — Steinfl & Bruno LLP

(57) ABSTRACT

A videorhinohygrometric measuring apparatus (1) for evaluating parameters associated to the expiratory flow outlet from the nostrils, comprising a camera (4) for acquiring the dynamic image of the condensation that the flow generates on a suitable collecting surface (21) and a processor (5) for the acquired image, operatively connected to the camera (4) and apt to output at least one of the above-mentioned entities.

25 Claims, 1 Drawing Sheet

(56) References Cited

OTHER PUBLICATIONS

Figure 1:
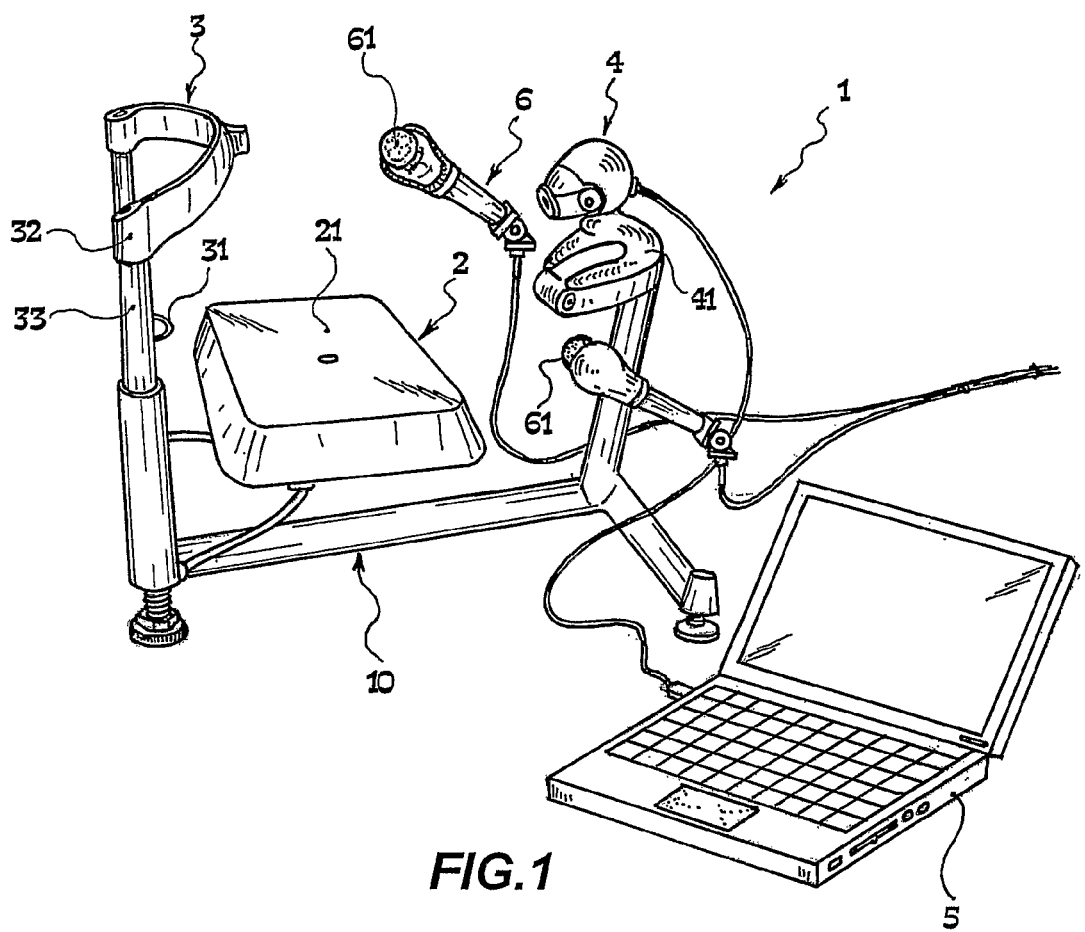

Lieb et al., Nasograph mirror of Glatzel as a measure of nasal patency, 1939, Archives of Otolaryngology, 30(3):334-343).*
Brescovici, "The Glatzel Mirror in the Assessment of Nasal Patency in Adults", 2004, Universidade Federal do Rio Grande do Sul, Masters Dissertation, p. 1-104.*
Brescovici et al., 2008, Modified glatzel mirror test reproducibility in the evaluation of nasal patency, 2008, Brazilian Journal of Otorhinolarngology, 74(2), 215-222.*
Nichols, Analytical Geometry: Chapter VII The Ellipse, D.C. Heath & Co., Revised Edition, 108-142.*
Casale et al., Video-Rhino-Hygrometer (VRH), 2006, Proceedings of the 28th IEEE EMBS Annual International Conference, 543-546.*
R. Gertner et al., "A simple method of measuring the nasal airway in clinical work", The Journal of Laryngology and Otology, vol. 98, Apr. 1984, pp. 351-355.

PCT International Search Report for PCT/IT2006/000251 filed on Apr. 13, 2006 in the name of Manuele Casale et al.
PCT Written Opinion of International Application PCT/IT2006/000251 filed on Apr. 13, 2006 in the name of Manuele Casale et al. Mail date: Feb. 12, 2007.
EP Communication from the Examining Division for application EP06745278.9 filed on Nov. 13, 2008 in the name of Manuele Casale et al. Mail date: Mar. 12, 2010.
Reply to EP Communication of Mar. 12, 2010 for application EP06745278.9 filed on Nov. 13, 2008 in the name of Manuele Casale et al. Date of submission: Sep. 22, 2010.
EP Communication from the Examining Division for application EP06745278.9 filed on Nov. 13, 2008 in the name of Manuele Casale et al. Mail date: Jun. 29, 2011.
Reply to EP Communication of Jun. 29, 2011 for application EP06745278.9 filed on Nov. 13, 2008 in the name of Manuele Casale et al. Date of submission: Dec. 20, 2011.

* cited by examiner

APPARATUS AND METHOD FOR VIDEORHINOHYGROMETRIC (VRI) MEASURES

CROSS REFERENCE TO RELATED APPLICATIONS

The present application is the US national stage of International Application PCT/IT2006/000251 filed on Apr. 13, 2006.

The present invention refers to an apparatus for videorhinohygrometric (VRI) measures and to a related method.

Nasal pathologies, and in particular deviations, or alterations in general of the nasal septum, have a significant impact on the respiratory function, and therefore, ultimately, on the life quality of persons affected thereby.

Over the years, various techniques for assessing such nasal septum deviations or alterations have been advanced, based on measures carried out from the outside and generally considering the inflow and/or outflow into/from the nostrils.

One of the earliest techniques is the so-called rhinometric or rhinohygrometric one, based on the fact that air expired from nostrils onto a surface produces "smudges" or "halos" due to the condensing of the steam contained just in the expired air. Qualitative observation of such halos has been employed to attain an approximate idea of nasal patency. This observation has been made partially quantitative by use of a graduated metal plate onto which condensation is to be collected, and then of a liquid-crystal plate producing a permanent recording of the final configuration of said halos.

The videorhinohygrometric technique entails the advantage, with respect to the others, of being extremely simple to use, inexpensive, non-invasive and rapid.

However, it still yields essentially qualitative and scarcely reproducible results and does not allow to discriminate in all cases and with certainty the flows corresponding to the two nostrils.

Hence, the technical problem set and solved by the present invention is to provide an apparatus and a method for VRI measures overcoming the drawbacks mentioned above with reference to the known techniques.

Such a problem is solved by an apparatus according to claim 1 and by a method according to claim 16.

Preferred features of the present invention are defined in the dependent claims thereof.

The present invention provides several relevant advantages. In particular, it is capable of providing quantitative evaluations that are accurate, reproducible and easily associable to the level of patency of the nasal cavities, as well as useful to assess possible alterations of the, nasal septum and, in general, the physiological or pathological state/condition of the same nasal structures.

Concomitantly, the apparatus and the method of the invention retain the properties of implementation simplicity, non-invasiveness, absolute non-alteration of the nasal ducts, rapidity and low cost of the basic rhinometric technique. Moreover, the invention allows an elevated automation level of the measures.

Figure 2:
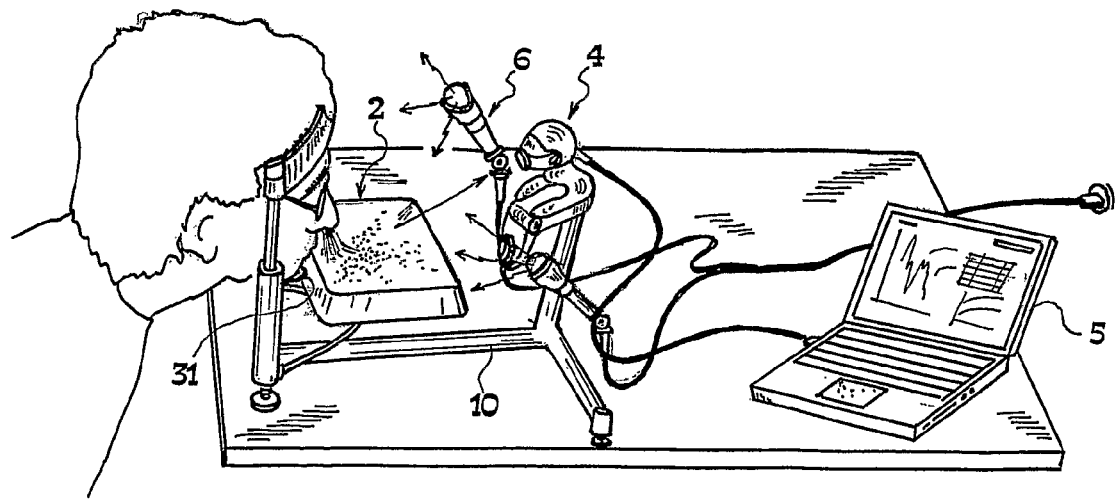

Other advantages, features and the operation modes of the present invention will be made evident in the following detailed description of some embodiments thereof, given by way of example and without limitative purposes. Reference will be made to the figures of the annexed drawings, wherein:

FIG. 1 shows a perspective view of a first embodiment of the apparatus of the present invention; and FIG. 2 shows an additional perspective view of the apparatus of FIG. 1 during use in a measuring session.

With reference to said figures, an apparatus for videorhinohygrometric measures according to a first embodiment of the invention is generally denoted by 1. According to the invention, the apparatus 1 is apt to evaluate parameters associated to the expiratory flow outlet from the nostrils.

The apparatus 1 comprises a condensation-collecting element, denoted by 2, in the form of a metal plate, in particular made of aluminum or stainless steel. Such a plate 2 has a substantially plane top surface 21, apt just to allow the condensing thereon of the steam contained in the expiratory flow of the two nostrils of a subject. In order to prevent measuring disturbances related to the lighting of the room and of the surface 21 itself, preferably the latter is anti-reflection, e.g. dull or dulled.

The apparatus also comprises means (not shown) for controlling the temperature of the surface 21, and in particular cooling means apt to hold such a temperature preferably in a range equal to about 7-10° C., and even more preferably equal to 7° C.

Preferably, the apparatus 1 includes also means (not shown) for metering the temperature and the humidity of air in the room, in particular a thermometer and a hygrometer, in order to use the data thus obtained to adjust and standardize the measures carried out on said condensation. Of course, the apparatus 1 may include also means for metering and indicating the temperature of the plate 2.

Moreover, the apparatus 1 comprises supporting means 3 apt to support and position the face of the subject on which the VRI examination is carried out, which in the present embodiment comprises a chin support (rest) 31 and a forehead support (rest) 32 connected by one or more vertical rods 33. Preferably, the latter are telescopic and therefore of adjustable length in order to allow an adaptation of the apparatus 1 to different casts of features.

The supporting means 3 may be of the type usually employed in eye examinations.

The provision of said supporting means 3 is relevant mainly for two reasons, one of a physiological nature and one of a technical nature. First of all, the neck of the subject under examination must be in a relaxed position, something not attainable without a chin rest, since a stiffening of the muscles would cause an obstruction of the venous flow and an entailed alteration of the nasal resistances. Moreover, the use of mere telescopic arms and/or of a mere worm screw mechanism for the adjusting of the support length and in particular of the position of the chin rest 31 with respect to the collecting surface 21 is a simple and cost-effective solution.

Also the collecting element 2 may comprise respective adjusting means (not shown) to allow to vary his/her own relative position with respect to the supporting means 3. In particular, the collecting element 2 may be shifted horizontally as well as vertically, e.g., by trolley mechanisms and/or prismatic guides so as to allow to adjust the instrument to patients of different morphology and constitution.

Likewise, also the supporting means 3 may provide means for adjusting the horizontal position thereof.

The apparatus 1 comprises also means 6 for lighting the collecting surface 21, which in the present embodiment is implemented by two lamps 61 arranged sideways to the surface 21 itself and apt to light it in a substantially uniform way. Preferably, also the relative position of said lamps with respect to the surface 21 is adjustable. In particular, the lamps 61 may be mounted on telescopic tubes, and therefore be adjustable in length, and/or on a structure allowing to translate them horizontally in the direction of the chin support 31 and/or to rotate them.

Moreover, the apparatus 1 comprises means 4 for acquiring dynamic images, in particular a camera or a so-called webcam, arranged so as to acquire the dynamic image of the condensation forming on the surface 21 as the subject goes on with the respiratory acts. This dynamic image, as mentioned above, is typically in the form of one or more halos.

Preferably, the camera 4 is mounted on a movable arm 41 allowing the motion thereof according to three degrees of freedom, two translational and one rotary.

The acquiring means 4 is operatively connected to processing means 5, implemented, e.g., by an electronic processor (computer), apt to carry out a dynamic analysis of the halos and output a plurality of parameters related to the expiratory flow. In the present embodiment, it is provided that the processing means 5 computes and outputs some parameters and indexes associated to the condensation halos of the right and left nostrils and the time pattern of some entities. In particular, the means 5 is apt to provide the following entities, in terms of mean values on the single respiratory act and on all the respiratory acts considered during the test, as well as in terms of time pattern:

areas of the halos corresponding to the two nostrils;
length of the major and minor axes of each area and orientation thereof;
ratio between instantaneous and mean areas of the two halos (nasal septum deviation index);
position of the mass centroid associated to each nostril;
coordinates of the principal inertial axes of said areas in a selected reference system, tilt of said axes with respect to a preset direction (e.g., the x-axis of said reference system) and, generally, spatial orientation thereof.

Moreover, the processing means 5 is apt to output the time difference between the maximum and minimum peak values of the surfaces of the two halos, the mean time of rise (and of descent) from the minimum value to the maximum value of each halo and the residence time of the maximum and the minimum value of the area of the halo.

The processing means may then be operatively connected to the above-introduced temperature and/or humidity metering means, as well as to said various means for adjusting the position of the supporting means 3, of the collecting element 2 and of the lighting system.

The apparatus 1 may also incorporate a control panel manageable by the operator, optionally implemented directly by an interface of the processing means 5.

In the present embodiment, all components, optionally with the exception of the processing means 5 that may be remotely connected to the acquiring means 3, are mounted on a same frame 10.

By now, the operation modes of the apparatus 1 will have been made evident. During the VRI examination, the subject rests the chin onto the chin support 31 in front of which the camera 4 is arranged, continually acquiring the image gradually forming onto the surface 21 of the plate 2. The latter is suitably lighted by the lamps of the lighting means 6 fixed on the frame 10 each at one side of the camera 4.

In order to obtain a reliable result, it is preferable to repeat the examination for various subsequent respiratory acts (at least five), so as to compute the pattern of the selected parameters as a function of time. On operator's instructions, the processing means 5 can also eliminate the first n seconds of recording (to avoid artifacts related to a patient's emotional phenomena) and automatically exclude from the analysis the last instants of recording, should the same belong to an incomplete respiratory act.

Upon acquiring the complete dynamic image of the halos related to a certain examination, or, if possible, even already during the carrying out thereof, the processing means 5 proceeds first of all to convert the dynamic image into gray scales.

Then, some morphological operations are carried out on the acquired dynamic image, e.g., erosion, dilation, filling and connection operations, so as to eliminate any noise and adequately single out the area of the halos. Said operations are known per se to a person skilled in the art, and implemented by software means within his/her reach, therefore they will not be further detailed hereinafter.

Then, the image is further processed to single out and partition the contribution of each nostril, i.e. to discriminate, for each frame, the halo corresponding to each nostril. Such a further processing may, e.g., be based on threshold segmentation algorithms, by applying first of all a so-called edge detection technique, per se well-known to a person skilled in the art, to single out the area of the halos, and then a so-called watershed segmentation technique to partition halos possibly overlapped in portions, or sub-portions, corresponding to a respective nostril. As it is known, this segmentation technique starts with a computing of the image gradient to get to the definition of a line partitioning the image into two zones. In particular, first-order derivatives may be used to detect significant discontinuities, using Sobel masks to approximate the 2-D gradient.

Thus, all artifacts (like, e.g., the patient's image reflected on the plate or other spurious elements) have been eliminated from the image and the contour of each one of the two halos has been identified.

Upon identifying for each frame the halo corresponding to each nostril, the above-mentioned parameters and entities, which may also be selected by the operator and be then provided in graphic form on paper medium, a video, etc., are computed.

For entities making reference to a "mass", the latter is obtained with reference to the gray levels of the pixels. E.g., the position of the center of mass of each halo is obtained as weighted mean on the gray value of the various pixels inside the halo.

The system also deducts the values thus obtained, with a suitable compensation table, so as to standardize the values in connection to the room temperature and humidity.

Said parameters and entities may then be used to infer quantitative information about the difference in expiratory flow between the two nostrils, the resistances therein and/or possible mono- or bilateral alterations. In particular, the ratio of the flows outlet from the two nostrils (usually evaluated in the known art through a so-called rhinomanometric examination) may be computed as ratio between the areas of the halos, and the presence, the extent and the putative causes of a possible deviation of the nasal septum may be related to the pattern over time of the position of the mass centroid and a comparative analysis of the flows.

Moreover, additional indications on the conditions of the nasal cavities may be provided from the comparison of the relative orientation of the axes of the two halos.

In addition, it is possible to desume information related to the shape and the absolute dimension of the flow, for an improved characterization of the quality and consistence of the respiratory act.

Moreover, the dynamic study of the invention allows to obtain more accurate information about the difference in area of the two halos from the right and left nostrils, linked, e.g., to a difference in patency between the two nasal cavities.

Experimental tests carried out by comparing the results obtained with the method and the apparatus described hereto to the outcome of traditional rhinomanometric examinations highlighted the capability of the invention to provide said indications about the physiologic or pathologic condition of the subject, as well as to be an extremely accurate and sensible measuring method. Such tests also confirmed how the extent of the flow outlet from each nostril is proportional to the area of the respective halo.

The present invention also relates to a method mainly providing the steps of:
  acquiring a dynamic image of the condensation that the expiratory flow generates on a suitable collecting surface 21; and
  processing the acquired dynamic image so as to provide at least one of the above-mentioned entities.

Such steps are preferably carried out in accordance with what has already been illustrated above in connection to the apparatus 1 of the invention; therefore, a further description thereof will be omitted.

The present invention has hereto been described with reference to preferred embodiments thereof. It is understood that there could be other embodiments referable to the same inventive kernel, all falling within the protective scope of the claims hereinafter.

The invention claimed is:

1. A videorhinohygrometric measuring apparatus adapted to evaluate entities associated with an expiratory flow outlet from the nostrils, comprising:
  a collecting surface adapted to receive condensation generated from an expiratory flow, the collecting surface comprising a dulled metallic material;
  a camera or a webcam for acquiring a dynamic image, configured to dynamically acquire the dynamic image of condensation that said expiratory flow generates on the collecting surface;
  a face support for supporting a subject's face while acquiring the dynamic image; and
  a processor configured for processing said dynamic image, operatively connected to said camera or said webcam and adapted to output at least one of the following entities:
  length of a major and a minor axes of each halo formed by said condensation and orientation thereof,
  ratio between instantaneous and mean areas of each halo corresponding the nostrils,
  position of a mass centroid associated with an area of the halo of the nostrils,
  coordinates of principal inertial axes of the areas of the halos in a selected reference system,
  tilt of said axes with respect to a preset direction,
  spatial orientation of said axes,
  time difference between a maximum value and a minimum value of the areas of said halos, time of rise from the minimum value to the maximum value, and residence time of the maximum value and the minimum value.

2. The apparatus according to claim 1, comprising adjusting means for adjusting a position of said camera or webcam with respect to said collecting surface.

3. The apparatus according to claim 1, wherein said processor is adapted to separate, in said dynamic image, a first halo corresponding to a first nostril from a second halo corresponding to a second nostril.

4. The apparatus according to claim 1, wherein said processor is adapted to provide, for at least one of said entities, a time pattern and/or a value for a single respiratory act and/or for all respiratory acts considered during a test.

5. The apparatus according to claim 1, wherein said processor is adapted to convert said dynamic image into gray scales.

6. The apparatus according to claim 1, comprising a collecting element bearing said collecting surface.

7. The apparatus according to claim 6, wherein said collecting element is plate-shaped.

8. The apparatus according to claim 1, comprising lighting elements for lighting said collecting surface.

9. The apparatus according to claim 8, wherein said lighting elements are configured to generate a uniform lighting of said collecting surface.

10. The apparatus according to claim 8, wherein said lighting elements comprise a pair of lighting elements arranged at opposite sides of said collecting surface.

11. The apparatus according to claim 8, comprising adjusting means for adjusting relative position of said lighting elements with respect to said collecting surface.

12. The apparatus according to claim 1, wherein said face support comprises a chin support arranged or adapted to be arranged substantially facing said collecting surface.

13. The apparatus according to claim 1, wherein said face support comprises a forehead support.

14. The apparatus according to claim 1, wherein said face support is an adjustable face support, the adjustable face support being adaptable to different facial features.

15. The apparatus according to claim 1, wherein a relative position of said face support is adjustable with respect to said collecting surface.

16. A videorhinohygrometric measuring method, adapted to evaluate entities associated with an expiratory flow outlet from the nostrils, comprising:
  providing a collecting surface, said collecting surface comprising a dulled metallic material;
  acquiring, through a camera or webcam, a dynamic image of condensation that said expiratory flow generates on the collecting surface;
  providing a face support for supporting a user's face while acquiring the dynamic image; and
  processing through a computer processor, the acquired dynamic image to output at least one or more of the following entities:
  length of major and minor axes of each halo formed by said condensation and orientation thereof,
  ratio between instantaneous and mean areas of the halos corresponding to the two nostrils,
  position of a mass centroid associated with an area of the halo of each nostril,
  coordinates of principal inertial axes of the areas of said halos in a selected reference system,
  tilt of said major and minor axes with respect to a preset direction,
  spatial orientation of said major and minor axes,
  time difference between a maximum value and minimum value of the areas of said halos, time of rise from the minimum value to the maximum value, and residence time of the maximum value and the minimum value.

17. The method according to claim 16, wherein said processing separates, in said dynamic image, a first halo corresponding to a first nostril from a second halo corresponding to a second nostril.

18. The method according to claim 16, wherein said processing provides, for at least one of said entities, a time pattern and/or a value for a single respiratory act and/or for all respiratory acts considered during a test.

19. The method according to claim 16, wherein said processing converts said dynamic image into gray scales.

20. The method according to claim 16, wherein the collecting surface is anti-reflection.

21. The method according to claim 16, wherein said face support comprises a chin support arranged or adapted to be arranged substantially facing said collecting surface.

22. The method according to claim 16, wherein said face support comprises a forehead support.

23. The method according to claim 16, wherein said expiratory flow is generated through a plurality of expiratory acts.

24. The method according to claim 16, further comprising maintaining a temperature of the collecting surface in a range of 7-10 degrees Celsius during use.

25. A videorhinohygrometric measuring apparatus adapted to evaluate entities associated with an expiratory flow outlet from the nostrils, comprising:
    a collecting surface adapted to receive condensation generated from an expiratory flow, the collecting surface comprising a dulled material;
    a camera or a webcam for acquiring a dynamic image, configured to dynamically acquire, from above the collecting surface, the dynamic image of condensation that said expiratory flow generates on the collecting surface;
    a face support for supporting a subject's face while acquiring the dynamic image; and
    a processor configured for processing said dynamic image, operatively connected to said camera or said webcam and adapted to output at least one of the following entities:
length of a major and a minor axes of each halo formed by said condensation and orientation thereof,
ratio between instantaneous and mean areas of each halo corresponding the nostrils,
position of a mass centroid associated with an area of the halo of the nostrils,
coordinates of principal inertial axes of the areas of the halos in a selected reference system,
tilt of said axes with respect to a preset direction,
spatial orientation of said axes,
time difference between a maximum value and a minimum value of the areas of said halos, time of rise from the minimum value to the maximum value, and residence time of the maximum value and the minimum value.

\* \* \* \* \*